United States Patent [19]

Retzer

[11] 4,104,025
[45] * Aug. 1, 1978

[54] METHOD OF PREPARING LIQUID SAMPLES FOR TESTING

[75] Inventor: Erich Retzer, Miasach, Germany

[73] Assignee: Compur-Werk Gesellschaft mit beschrankter Haftung & Co., Munich, Germany

[ * ] Notice: The portion of the term of this patent subsequent to Nov. 16, 1993, has been disclaimed.

[21] Appl. No.: 732,217

[22] Filed: Oct. 14, 1976

[30] Foreign Application Priority Data

Nov. 28, 1975 [DE] Fed. Rep. of Germany ....... 2553613

[51] Int. Cl.$^2$ .................. A61B 10/00; B01L 3/02; G01N 1/10; G01N 33/16

[52] U.S. Cl. ............... 23/230 R; 23/230 B; 23/253 R; 23/259; 73/425.4 P; 128/2 F; 128/DIG. 5; 210/DIG. 23; 356/246

[58] Field of Search ............ 23/230 R, 230 B, 253 R, 23/259, 292; 73/425.4 P; 356/246 (U.S. only); 128/2 F, 2 G, DIG. 5; 210/DIG. 23

[56] References Cited

U.S. PATENT DOCUMENTS

| 3,475,127 | 10/1969 | Gilford | 23/230 R |
| 3,570,314 | 3/1971 | Wagner | 23/253 R X |
| 3,983,037 | 9/1976 | Lee et al. | 23/259 X |
| 3,992,150 | 11/1976 | Retzer | 23/230 R |
| 4,024,857 | 5/1977 | Blecher et al. | 23/259 X |

Primary Examiner—Joseph Scovronek
Attorney, Agent, or Firm—Stonebraker, Shepard & Stephens

[57] ABSTRACT

A method of preparing samples for testing, such as blood samples for photometric testing. A small quantity of the material to be tested, such as blood, is drawn into a capillary tube. The tube is then placed in a centrifuge and subjected to the action of centrifugal force which separates the test substance within the tube into a heavier component at one end of the tube and a lighter component at the other end. A second capillary tube, having an external diameter slightly less than the internal diameter of the first tube, is then introduced into the first tube and, by capillary action, picks up a definite measured quantity of the desired component from the first tube. The second tube, with the measured quantity of desired component therein, is placed in a cuvet previously provided with a predetermined quantity of a desired reagent liquid, and the cuvet is then shaken to disperse the contents of the second capillary tube into the reagent liquid in the cuvet. The thoroughly mixed contents of the cuvet are then ready for testing in any desired way, such as by use of a photometer.

7 Claims, 6 Drawing Figures

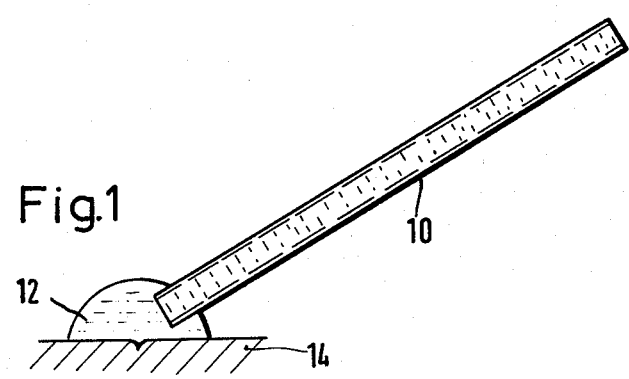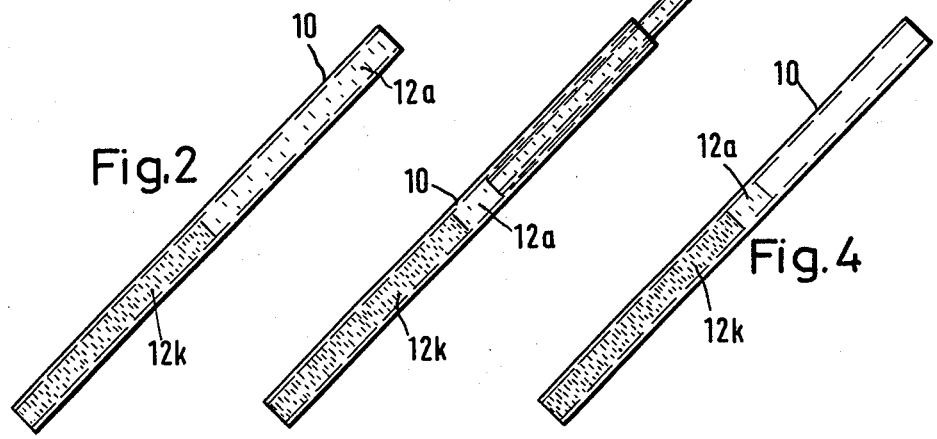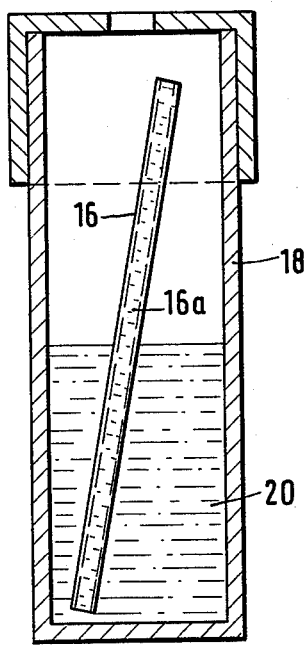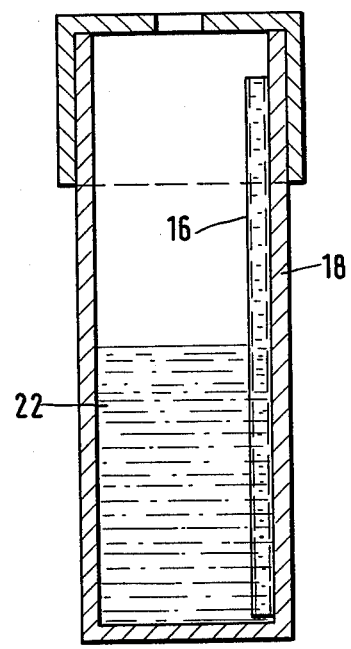

METHOD OF PREPARING LIQUID SAMPLES FOR TESTING

BACKGROUND OF THE INVENTION

In the prior practice, the preparation of samples for testing, particularly blood samples for photometric testing, has been a complicated and time consuming process, requiring large quantities of blood and expensive equipment. For example, in the prior practice a large quantity of blood is extracted from a vein of the patient, by an extraction vessel consisting of a cannula and a blood pump. Then a part of the extracted quantity of blood is placed in a centrifuging apparatus and centrifuged to separate the substance to be tested. After this separation process, a predetermined quantity of the separated substance is extracted by means of a dispensing appliance, for example a pipette, and is mixed in a cuvet with a predetermined preparation of reactive liquid to form the required measuring or testing fluid. This known method thus requires expensive transfer equipment and involves the problem of keeping the transfer equipment (including pipettes, for example) clean and sanitary for repeated use.

An object of the present invention is to eliminate the drawbacks of the conventional method, greatly simplifying the procedure as well as employing equipment which can be produced sufficiently cheaply so that it may be used only once and then discarded, eliminating the need for cleaning and sterilizing it for reuse.

BRIEF DESCRIPTION OF THE DRAWINGS

FIG. 1 is a schematic illustration of the first capillary tube in the process of extracting blood;

FIG. 2 is a schematic view of the same tube after it has been subjected to a centrifuging action to separate the contents into its components;

FIG. 3 is a schematic illustration of the method step in which a second capillary tube is introduced into the first capillary tube to extract therefrom a measured quantity of the desired component;

FIG. 4 illustrates the contents remaining in the first capillary tube after the desired quantity of a separated component has been extracted by the second capillary tube;

FIG. 5 illustrates the placing of the second capillary tube in a cuvet having a measured quantity of reagent liquid, to be shaken to mix the contents of the second capillary tube with the reagent liquid; and FIG. 6 illustrates the cuvet containing the mixture of the contents of the capillary tube with the reagent liquid, ready for testing.

DESCRIPTION OF THE PREFERRED METHOD

According to the method of the present invention, when a sample of a substance is to be prepared for photometric or other testing, for example a sample of blood plasma or blood serum, only a small quantity of blood is extracted (FIG. 1) by capillary action, by means of a first capillary tube 10 brought into contact with a drop of blood 12 produced by opening, for example, the finger tip 14 of the patient. The blood from the drop fills the capillary tube 10 by capillary action.

The capillary tube 10 filled with blood (or any other substance to which the method is applicable) is then clamped in a centrifuge (which may be conventional, and is not illustrated here) with the tube in a radial direction with respect to the axis of rotation of the centrifuge. It is subjected to the centrifuging action for a predetermined length of time. This separates the contents of the capillary tube 10 into its components, for example (in the case of blood) into a blood plasma component 12a at one end of the tube 10 and a blood clot component 12k at the other end.

The operator now takes a second capillary tube 16, the outer diameter of which is slightly smaller than the inner diameter of the first tube 10, and introduces this second capillary tube 16 into the column 12a of blood plasma in the first tube, as illustrated in FIG. 3. By capillary action an exactly defined quantity of blood plasma 16a is transferred from the first capillary tube 10 into the second capillary tube 16, the exact quantity being determined by the internal diameter and the length of the second tube 16, since it becomes completely filled by the capillary action. Only the blood clot material 12k and the residue or excess quantity of blood plasma 12a remain in the first capillary tube, as illustrated in FIG. 4. This first tube may now be discarded, unless it is desired to make other tests involving the blood clot material 12k.

The second tube 16, containing the exact measured quantity of blood plasma 16a, is now introduced into a cuvet 18 previously charged with a predetermined quantity of reagent liquid 20 as illustrated in FIG. 4. The cuvet with the capillary tube 16 therein is then shaken for a sufficient time to mix the blood plasma 16a from the capillary tube thoroughly and uniformly with the reagant liquid 20, resulting in a mixture of the blood plasma and the reagent liquid as indicated at 22 in FIG. 6. The cuvet 18 containing this mixture 22 is now ready for testing in any desired way by any desired known method, such as photometric testing by the use of a photometer of known type and known operating procedure. It may be, for example, a conventional laboratory photometer, or it may be a small hand held photometer for possible emergency use in the field, such a photometer being disclosed in the copending patent application of Erich Retzer et al., Ser. No. 579,676, filed May 21. 1975 now U.S. Pat. No. 4,003,662, granted Jan. 18, 1977.

The cuvet 18 may be of any known form, for example, the form of cuvet disclosed in my copending patent application Ser. No. 572,222, filed Apr. 28, 1975, now U.S. Pat. No. 3,992,150, granted Nov. 16, 1976, or the improved form of cuvet disclosed in my copending patent application Ser. No. 701,079, filed June 30, 1976, now abandoned.

The two capillary tubes 10 and 16 may be made of any suitable transparent material, such as glass or plastic material, and have well defined dimensions. For example, they may have a length of 32 millimeters, the first capillary tube 10 having an inner diameter of 1.0 millimeters, and the second capillary tube 16 having an outer diameter of 0.8 millimeters.

It is readily seen that only a minimum quantity of blood is required for the performance of the method of the present invention, because there is no question of any loss during transference from one container or vessel to another. Moreover, no measurement of quantities is required in the intermediate stage of the method, since the quantities are automatically measured by the capacity of the respective capillary tubes. Finally, only two capillary tube are required as ancillary means, and these are sufficiently inexpensive when mass produced so that they may be regarded as one-time or throwaway disposable elements. The cuvets 18 may likewise be used only a single time and then thrown away, if desired.

Another aspect of the invention is the provision of the necessary equipment (except for the centrifuge and the photometer) in kit form, easily carried by the physician or technician, and containing all necessary elements. The kit may be, for example, the same as illustrated in FIGS. 1 and 2 of my above mentioned copending application Ser. No. 572,222, except that the capillary tubes 10 and 16 of both sizes would be included in the kit, instead of merely capillary tubes of one size. The cuvets included in the kit may be either of the original form disclosed in my above mentioned application Ser. No. 572,222 or of the improved form disclosed in my above mentioned application Ser. No. 701,079.

What is claimed is:

1. The method of preparing a liquid sample for testing which comprises the steps of
    (a) introducing a quantity of a liquid substance to be tested into a first capillary tube by capillary action,
    (b) subjecting the liquid contents of said first tube to centrifugal force exerted in a direction longitudinally of said first tube for a sufficient time to separate said contents into a plurality of components,
    (c) thereafter introducing into said first tube a second capillary tube whose external diameter is smaller than the internal diameter of said first tube and allowing capillary action to draw into said second tube a predetermined measured quantity of one of said components in the first tube,
    (d) providing a cuvet with a predetermined measured quantity of a reagent liquid,
    (e) placing said second tube with said one of said components therein into said cuvet with said reagent liquid therein, and
    (f) mixing the component from said second tube with the reagent liquid in said cuvet, thereby to form in said cuvet a mixture of reagent liquid and selected component from the original substance, ready for testing.

2. The method of claim 1, wherein said substance to be tested is blood.

3. The method of claim 1, wherein the measured quantity drawn into said second tube is the quantity required to fill said second tube completely.

4. The method of claim 1, wherein the component from said second tube is mixed with the reagent liquid in said cuvet by the act of shaking said cuvet.

5. The method of claim 1, wherein said one of said components drawn into said second tube is blood plasma.

6. The method of claim 1, wherein the testing of the mixture formed in said cuvet is photometric testing.

7. A portable kit for preparing a liquid sample for subsequent testing, said kit comprising, in combination, a cuvet having a predetermined quantity of a reagent liquid therein, a first capillary tube adapted to receive, by capillary action, a quantity of a liquid substance to be tested and adapted to be subjected to centrifugal foce to separate the contents of the first tube into components, and a second capillary tube having an external diameter smaller than the internal diameter of the first tube and adapted to be inserted into the first tube to draw therefrom, by capillary action, a predetermined measured quantity of a component from the first tube, said second tube being adapted to be placed in said cuvet to transfer to the cuvet the contents of the second tube, to be mixed with the reagent liquid therein.

* * * * *